United States Patent
Dyballa et al.

(10) Patent No.: US 10,526,356 B2
(45) Date of Patent: Jan. 7, 2020

(54) BISPHOSPHITES HAVING 2,4-TERT-BUTYLPHENYL UNITS AND USE THEREOF AS LIGANDS IN HYDROFORMYLATION

(71) Applicant: EVONIK DEGUSSA GMBH, Essen (DE)

(72) Inventors: Katrin Marie Dyballa, Recklinghausen (DE); Robert Franke, Marl (DE); Dirk Fridag, Haltern am See (DE); Dieter Hess, Marl (DE)

(73) Assignee: EVONIK DEGUSSA GMBH, Essen (DE)

(*) Notice: Subject to any disclaimer, the term of this patent is extended or adjusted under 35 U.S.C. 154(b) by 0 days.

(21) Appl. No.: 15/805,401

(22) Filed: Nov. 7, 2017

(65) Prior Publication Data

US 2018/0127444 A1    May 10, 2018

(30) Foreign Application Priority Data

Nov. 8, 2016    (EP) ..................... 16197715

(51) Int. Cl.
| | | |
|---|---|---|
| *C07F 9/141* | (2006.01) | |
| *B01J 31/18* | (2006.01) | |
| *C07C 45/50* | (2006.01) | |
| *C07F 15/00* | (2006.01) | |
| *C07F 9/145* | (2006.01) | |

(52) U.S. Cl.
CPC .......... *C07F 9/141* (2013.01); *B01J 31/185* (2013.01); *C07C 45/50* (2013.01); *C07C 45/505* (2013.01); *C07F 9/145* (2013.01); *C07F 15/008* (2013.01); *C07F 15/0073* (2013.01); *B01J 2231/321* (2013.01); *B01J 2531/822* (2013.01)

(58) Field of Classification Search
None
See application file for complete search history.

(56) References Cited

U.S. PATENT DOCUMENTS

| | | | |
|---|---|---|---|
| 4,769,498 A | 9/1988 | Billig et al. | |
| 5,235,113 A | 8/1993 | Sato et al. | |
| 5,719,312 A * | 2/1998 | Hansen ................ | C07C 51/373 560/177 |
| 5,723,641 A | 3/1998 | Tam et al. | |
| 5,910,600 A | 6/1999 | Urata et al. | |
| 8,513,469 B2 | 8/2013 | Brammer | |
| 9,127,030 B2 | 9/2015 | Kreidler et al. | |
| 9,556,096 B2 | 1/2017 | Christiansen et al. | |
| 9,670,108 B2 | 6/2017 | Dyballa et al. | |
| 9,790,244 B2 | 10/2017 | Dyballa et al. | |
| 2016/0159839 A1 | 6/2016 | Dyballa et al. | |
| 2017/0129838 A1 | 5/2017 | Dyballa et al. | |
| 2017/0275316 A1 | 9/2017 | Dyballa et al. | |

FOREIGN PATENT DOCUMENTS

| | | |
|---|---|---|
| CN | 1141030 A | 1/1997 |
| CN | 1167769 A | 12/2017 |
| EP | 0 518 241 A2 | 12/1992 |
| JP | H05-178779 A | 7/1993 |
| JP | H09-507223 A | 7/1997 |
| TW | 213465 B | 9/1993 |
| TW | 201035033 A | 10/2010 |
| WO | 95/18089 A1 | 7/1995 |
| WO | 96/11182 A1 | 4/1996 |
| WO | 99/38832 A1 | 8/1999 |
| WO | 2012/095253 A1 | 7/2012 |
| WO | 2014/056733 A1 | 4/2014 |

OTHER PUBLICATIONS

Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts. Pure Appl. Chem., 2001, vol. 73, pp. 1795-1818.
Harris, Robin K. et al. Further Conventions for NMR Shielding and Chemical Shifts. Pure Appl. Chem., 2008, vol. 80, pp. 59-84.
European Search Report dated Apr. 21, 2017 for EP 16 19 7715 (1 page).
R. Franke, D. Selent, A. Börner, "Applied Hydroformylation", Chem. Rev. 2012, 112, pp. 5675-5732.
Search Report dated Nov. 13, 2018 in Taiwan Patent Application No. 106138090 (1 page in Chinese).
Office Action dated Dec. 12, 2018 in Korean Patent Application No. 10-2017-0147015 (4 pages in Korean with English translation).

* cited by examiner

*Primary Examiner* — Clinton A Brooks
(74) *Attorney, Agent, or Firm* — Smith, Gambrell & Russell, LLP

(57) ABSTRACT

The invention relates to bisphosphites having 2,4-tert-butylphenyl units and a method for the preparation thereof. Furthermore, the invention relates to the use of the compounds as ligands in a ligand-metal complex. The compound, and also the complex, may be used as a catalytically active composition in hydroformylation reactions.

13 Claims, No Drawings

BISPHOSPHITES HAVING 2,4-TERT-BUTYLPHENYL UNITS AND USE THEREOF AS LIGANDS IN HYDROFORMYLATION

The invention relates to bisphosphites having 2,4-tert-butylphenyl units and a method for the preparation thereof. Furthermore, the invention relates to the use of the compounds as ligands in a ligand-metal complex. The compound, and also the complex, may be used as a catalytically active composition in hydroformylation reactions.

Phosphorus-containing compounds, as ligands, play a crucial role in a multitude of reactions. Said compounds include phosphite ligands, i.e., compounds comprising P—O bonds, used in hydrogenation, hydrocyanation and especially hydroformylation.

The reactions between olefin compounds, carbon monoxide and hydrogen in the presence of a catalyst to give the aldehydes comprising one additional carbon atom are known as hydroformylation or oxo synthesis. In these reactions, compounds of the transition metals of group VIII of the Periodic Table of the Elements are frequently employed as catalysts. Known ligands include, for example, compounds of the phosphine, phosphite and phosphonite classes each comprising trivalent phosphorus $P^{III}$. A good overview of the status of hydroformylation of olefins is found in R. Franke, D. Selent, A. Börner, "Applied Hydroformylation", Chem. Rev., 2012, DOI: 10.1021/cr3001803.

The literature discloses the synthesis of symmetric bisphosphites, as disclosed in U.S. Pat. No. 4,769,498 for example, and the use thereof in catalytically active transition metal-containing compositions for the hydroformylation of unsaturated compounds.

In U.S. Pat. No. 4,769,498, and also in U.S. Pat. No. 5,723,641, preferably symmetric bisphosphites are prepared and used as ligands for hydroformylation. The symmetric bisphosphite ligands used in the hydroformylation are prepared at low temperatures. Adherence to these low temperatures is absolutely necessary since according to these US documents higher temperatures would lead to rearrangements and ultimately to asymmetric bisphosphites.

One ligand which affords a very good yield is the ligand according to formula (2):

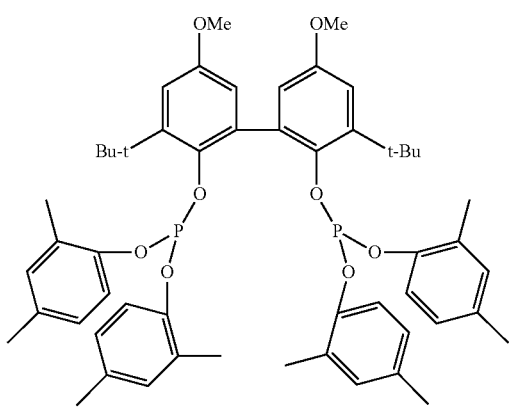

(2)

In the hydroformylation of raffinate 3, the ligand (2) however affords almost exclusively (to 99%) the n-pentanal. Raffinate 3 is a mixture of: ca. 26% 1-butene, 32% trans-2-butene, 17% cis-2-butene, 25% n-butane and traces of isobutane and neopentane.

For some technical applications, however, it is desirable that the ratio of linear aldehyde (=n-aldehyde) to branched aldehyde) (=isoaldehyde) is equalized as far as possible.

Definition of the Selectivity:

in hydroformylation, there is the n/iso selectivity: the ratio of linear aldehyde (=n) to branched aldehyde (=iso). In this case, the regioselectivity with respect to the n-aldehyde signifies that this amount of linear product was formed. The remaining percentage then corresponds to the branched isomer. Thus, at a regioselectivity of 50%, n-aldehyde and isoaldehyde are formed in equal proportions.

The technical object of the invention is the provision of a novel ligand which does not have the above-detailed disadvantages from the prior art in the hydroformylation of unsaturated compounds, but instead has the following properties:
1) a good activity/yield,
2) an n-regioselectivity with respect to hydroformylation of 50%+/− 15%.

The object is achieved by a compound according to Claim 1.

Compound of the formula (I):

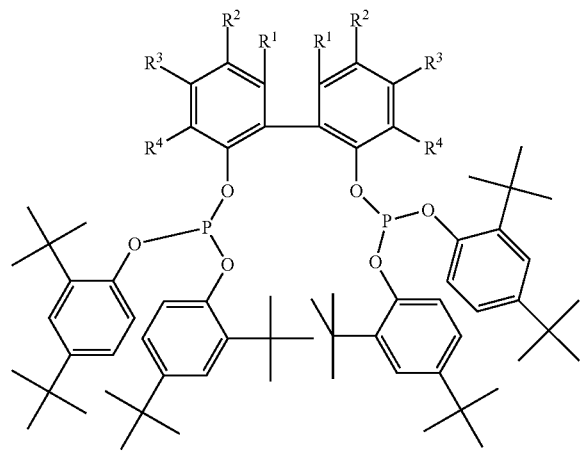

(I)

where
$R^1$, $R^2$, $R^3$, $R^4$ are selected from: —H, —($C_1$-$C_{12}$)-alky, —O—($C_1$-$C_{12}$)-alkyl,
wherein the alkyl groups mentioned may be substituted as follows:
substituted —($C_1$-$C_{12}$)-alkyl groups and substituted —($C_1$-$C_{12}$)-alkoxy groups, depending on their chain length, may have one or more substituents; the substituents are mutually independently selected from —($C_3$-$C_{12}$)-cycloalkyl, —($C_3$-$C_{12}$)-heterocycloalkyl, —($C_8$-$C_{20}$)-aryl, fluorine, chlorine, cyano, formyl, acyl or alkoxycarbonyl;
and at least on of the $R^1$, $R^2$, $R^3$, $R^4$ radicals is not —H.

In the context of the invention, the expression "—($C_1$-$C_{12}$)alky;" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—$(C_1-C_{12})$-alkyl" also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups, depending on their chain length, may have one or more substituents; the substituents are mutually independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

In one embodiment $R^2$, and $R^4$ are not —H.

In one embodiment, $R^2$ and $R^4$ are selected from: —$(C_1-C_{12})$-alkyl, —O—$(C_1-C_{12})$-alkyl.

In one embodiment, $R^2$ is —O—$(C_1-C_{12})$-alkyl.

In one embodiment, $R^4$ is —$(C_1-C_{12})$-alkyl.

In one embodiment, $R^1$, $R^2$, $R^3$, $R^4$ are selected from: —H, -Me, -tBu, —OMe, -iPr.

In one embodiment, $R^1$ is —H.

In one embodiment, $R^2$, $R^4$ are selected from: -Me, -tBu, —OMe, -iPr.

In one embodiment, $R^2$, $R^4$ are selected from: -Me, -tBu, —OMe.

In one embodiment, $R^2$ is selected from: -Me, -tBu, —OMe.

In one embodiment, $R^2$ is selected from: -tBu, —OMe.

In one embodiment, $R^2$ is selected from: -Me, —OMe.

In one embodiment, $R^2$ is —OMe.

In one embodiment, $R^3$ is —H.

In one embodiment, $R^4$ is selected from: -Me, -tBu, —OMe.

In one embodiment, $R^4$ is selected from: -tBu, —OMe.

In one embodiment, $R^4$ is selected from: -Me, -tBu.

In one embodiment, $R^4$ is -tBu

In one embodiment, the compound has the formula (1):

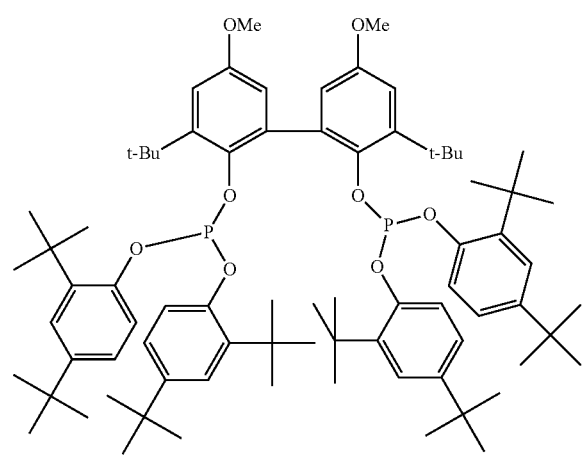

(1)

As well as the compounds, also claimed are complexes comprising the compound.

Complex according to the formula (II):

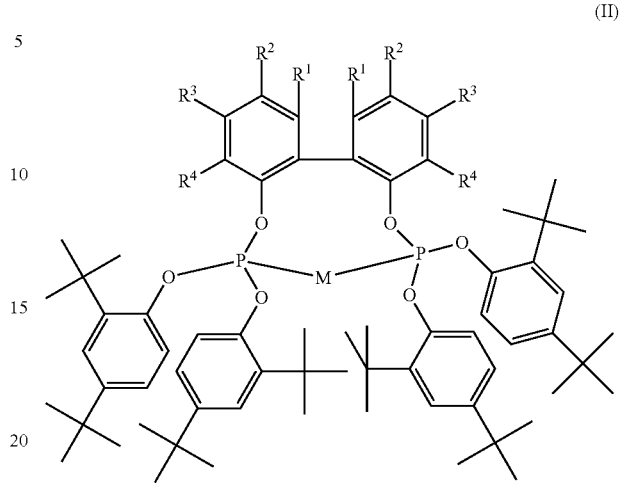

(II)

where
$R^1$, $R^2$, $R^3$, $R^4$ are selected from: —H, —$(C_1-C_{12})$-alkyl, —O—$(C_1-C_{12})$-alkyl, wherein the alkyl groups mentioned may be substituted as follows:

substituted —$(C_1-C_{12})$-alkyl groups and substituted —$(C_1-C_{12})$-alkoxy groups, depending on their chain length, may have one or more substituents; the substituents are mutually independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl;

and M is selected from: Rh, Ru, Co, Ir.

In a preferred embodiment, M=Rh.

The embodiments and selection options for the radicals $R^1$, $R^2$, $R^3$, $R^4$ cited above in conjunction with formula (I) apply analogously to formula (II).

Complex according to the formula (III):

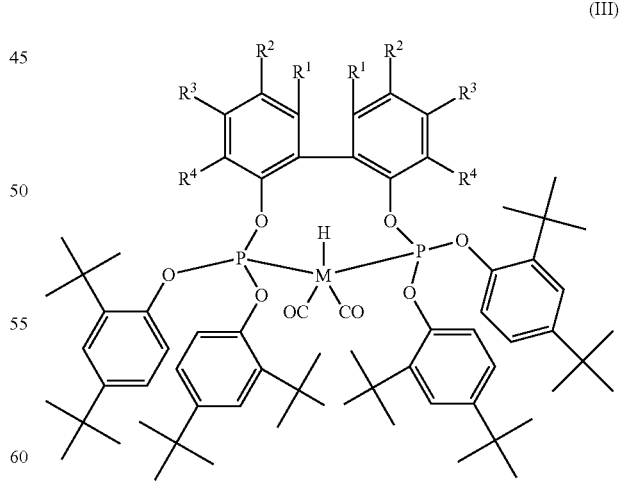

(III)

where
$R^1$, $R^2$, $R^3$, $R^4$ are selected from: —H, —$(C_1-C_{12})$-alkyl, —O—$(C_1-C_{12})$-alkyl, wherein the alkyl groups mentioned may be substituted as follows:

substituted —($C_1$-$C_{12}$)-alkyl groups and substituted —($C_1$-$C_{12}$)-alkoxy groups, depending on their chain length, may have one or more substituents; the substituents are mutually independently selected from —($C_3$-$C_{12}$)-cycloalkyl, —($C_3$-$C_{12}$)heterocycloalkyl, —($C_6$-$C_{20}$)-aryl, fluorine, chlorine, cyano, formyl, acyl or alkoxycarbonyl;

and M is selected from: Rh, Ru, Co, Ir.

In a preferred embodiment, M=Rh.

The embodiments and selection options for the radicals $R^1$, $R^2$, $R^3$, $R^4$ cited above in conjunction with formula (I) apply analogously to formula (III).

In addition to the compound and the complexes comprising the compound, the use of compound (I) and the complexes (II) or (III) for catalysis of a hydroformylation reaction is also claimed.

Use of the compound (I) in a ligand-metal complex for catalysis of a hydroformylation reaction.

Use of the complex (II) for catalysis of a hydroformylation reaction.

Use of the complex (III) for catalysis of a hydroformylation reaction.

Furthermore, the hydroformylation process is also claimed in which the compound (I) or the complex (II) or (III) is used.

Process comprising the following process steps:
a) initially charging an olefin,
b) adding an above-described complex,
or an above-described compound and a substance including a metal selected from: Rh, Ru, Co, Ir,
c) feeding in $H_2$ and CO,
d) heating the reaction mixture, wherein the olefin is converted to an aldehyde.

Process steps a) to c) can be carried out here in any desired sequence.

The compound may be used as a ligand in a ligand-metal complex.

An excess of ligands can also be used in this case and each ligand is not necessarily present bound in the form of a ligand-metal complex but is present as free ligand in the reaction mixture.

The reaction is conducted under customary conditions.

Preference is given to a temperature of 80° C. to 160° C. and a pressure of 1 to 300 bar.

Particular preference is given to a temperature of 100° C. to 160° C. and a pressure of 15 to 250 bar.

In a preferred embodiment, the metal is Rh.

The reactants for the hydroformylation in the process of the invention are olefins or mixtures of olefins, especially monoolefins having 2 to 24, preferably 3 to 16 and particularly preferably 3 to 12 carbon atoms, having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_8$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures prepared by cooligomerization of olefins having different numbers of carbon atoms (preferably 2 to 4).

The process according to the invention using the ligands according to the invention can be used to hydroformylate α-olefins, terminally branched, internal and internally branched olefins.

The invention is to be illustrated in greater detail hereinafter by working examples.

General Procedure Specifications

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}$P NMR signals were referenced as follows: $SR_{31P}=SR_{1H}*(BF_{31P}/BF_{1H})=SR_{1H}*0.4048$ (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

General Reaction Equation (Comparative Ligand)

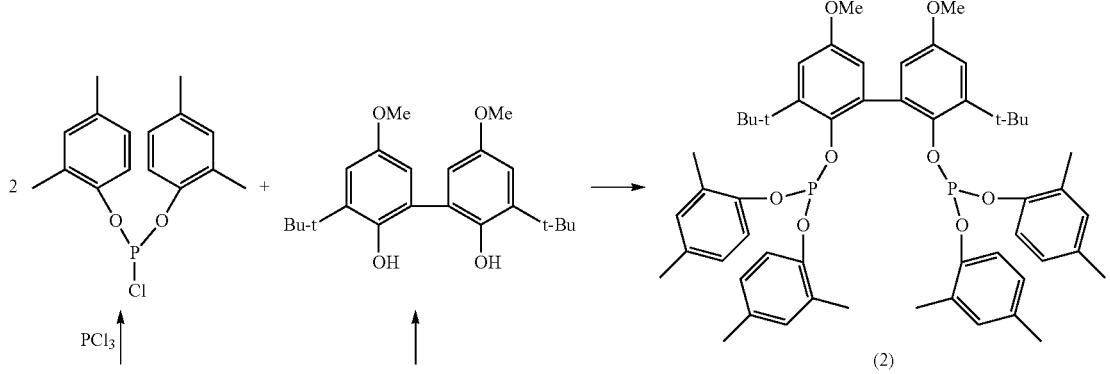

(2)

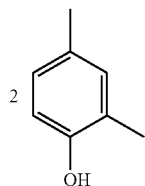 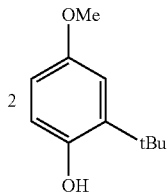

Preparation of bis(2,4-dimethylphenyl)chlorophosphite

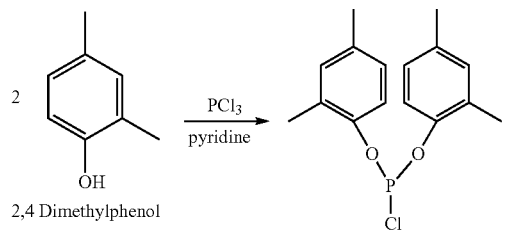
2,4 Dimethylphenol 50 g of PCl₃ (0.363 mol) and 86 g of pyridine (1.076 mol) in 380 ml of dry toluene were initially charged in a secured 1200 ml glass reactor provided with a dropping funnel. The milky yellow PCl₃/pyridine solution was cooled down to −7° C. with stirring. 86 ml of 2,4-dimethylphenol (0.720 mol) were then added to the dropping funnel and dissolved in 380 ml of dry toluene. To carry out the reaction, the phenol/toluene solution was added dropwise slowly and steadily to the PCl₃/pyridine solution. The reaction mixture was brought to room temperature overnight with stirring.

For workup, the hydrochloride formed was filtered off and rinsed with 60 ml of dry toluene and the resulting mother liquor was concentrated to dryness under reduced pressure.

For further work-up, the crude solution was distilled. For this purpose, a pear-shaped flask was filled with the crude solution, on which flask a short distillation apparatus without cooling jacket was placed. The thermometer was placed at the upper opening, and at the other end a spider with four further pear-shaped flasks was attached. Subsequently, this apparatus was attached to a cold trap and from there to the high vacuum pump. The pear-shaped flask with the crude ligand to be distilled was heated by means of an oil bath. Firstly, the forerun was removed at a top temperature of 25-30° C. The spider was then further rotated and the main run was removed at a top temperature of 140° C. When no more drops appeared in the main run, the distillation was stopped, the pump was shut down and the main run in the relevant pear-shaped flask was removed, sealed and analysed.

Result:
Total mass: 56.7 g (46% yield)

Preparation of 3,3'-di-tert-butyl-5,5'-dimethoxy-[1,1'-biphenyl]-2,2'-diyltetrakis(2,4-dimethylphenyl)bis(phosphite)

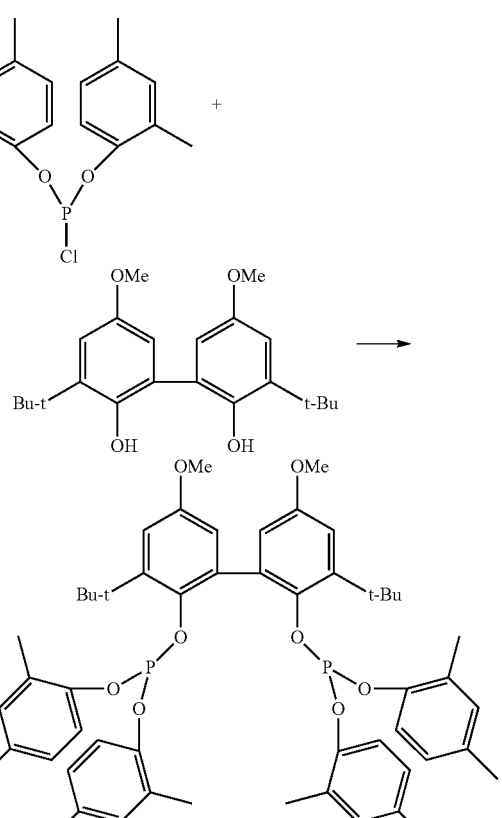

In a 1000 mL Schlenk flask, 260 ml of dry acetonitrile were added to 51.86 g (0.153 mol) of bis(2,4-dimethylphenyl)chlorophosphite at room temperature with stirring and the chlorophosphite was dissolved.

In a second 250 ml Schlenk flask, 12.4 ml (0.153 mol) of pyridine and 155 ml of dry acetonitrile were added to 20.1 g (0.056 mol) of 3,3'-di-tert-butyl-5,5'-dimethoxy-[1,1'-biphenyl]-2,2'-diol. The chlorophosphite solution in the Schlenk flask was then cooled to 0° C. The biphenol/pyridine solution was then slowly added dropwise with vigorous stirring. The reaction mixture was maintained at this temperature for ca. 3 h and then very slowly brought to room temperature overnight.

The suspension was then filtered off, washed thoroughly with 30 ml of acetonitrile and dried.
Result:
Mass: 44.01 g (yield: 85%)
Reduction of Chlorine Level
In order to decrease the chlorine content in this crude ligand, this ligand was purified.
The chlorine contents reported are meant as total chlorine contents.
The total chlorine content is determined according to Wickbold: sample preparation according to DIN 51408 and analysis by ion chromatography according to DIN EN ISO 10304.

5.15 g of 3,3'-di-tert-butyl-5,5'-dimethoxy-[1,1'-biphenyl]-2,2'-diyltetrakis(2,4-dimethylphenyl)bis(phosphite) in a 250 ml Schlenk flask with 15 ml of degassed toluene and 5 ml of pyridine at 100° C. were stirred until all had dissolved. After all had dissolved, the temperature was maintained for a further 15 min and then cooled to 90° C.

Meanwhile, 100 ml of heptane and 5 ml of pyridine were placed in another 250 ml Schlenk flask and the solution was cooled down to 0° C. Subsequently, the solution with the 3,3'-di-tert-butyl-5,5'-dimethoxy-[1,1'-biphenyl]-2,2'-diyltetrakis(2,4-dimethylphenyl)bis(phosphite) was added via the frit to the cold heptane/pyridine solution and stirred at 0° C. for 3 h. Here too, nothing precipitated out. Thus here also, by means of a vacuum pump, the solvent was drawn off until the solid had precipitated and was dried. 50 ml of acetonitrile were then added to the dry solid. This suspension was stirred at room temperature for two days, filtered off on a frit and dried by means of a vacuum pump.
Result:
Mass: 3.7 g
Chlorine determination: 20/20 ppm
General Reaction Equation (Inventive Ligand)

Preparation of Bis(2,4-tert-butylphenyl)chlorophosphite

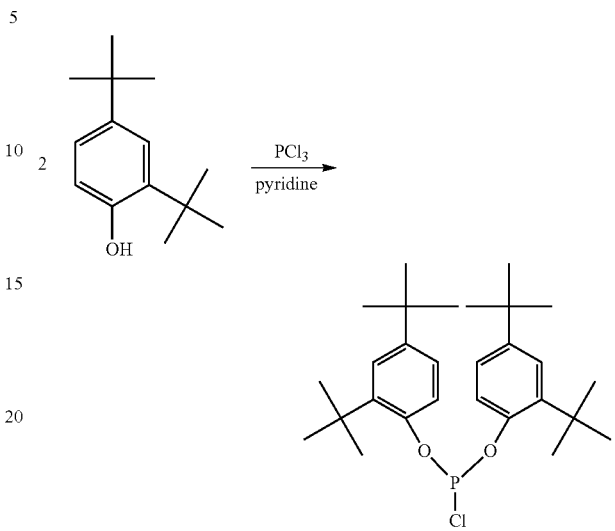

240 ml of dry toluene and 8.8 ml of phosphorus trichloride were initially charged in a secured 2000 ml Schlenk flask provided with a dropping funnel and cooled to 0° C. with stirring.

41.6 g of 2,4-di-tert-butylphenol were weighed out in a second 1000 ml Schlenk flask, dissolved in 415 ml of dry toluene and 100 ml of triethylamine were added.

The phenol/triethylamine solution was then transferred to the dropping funnel. The phenol/triethylamine solution was then added dropwise to the well-cooled toluene/phosphorus trichloride solution over 4 h with vigorous stirring. Here, care was takers to maintain a constant drop rate of one drop per second. Subsequently, the mixture was heated to room temperature and stirred for 12 hours, then heated to 45° C. for 4 hours.

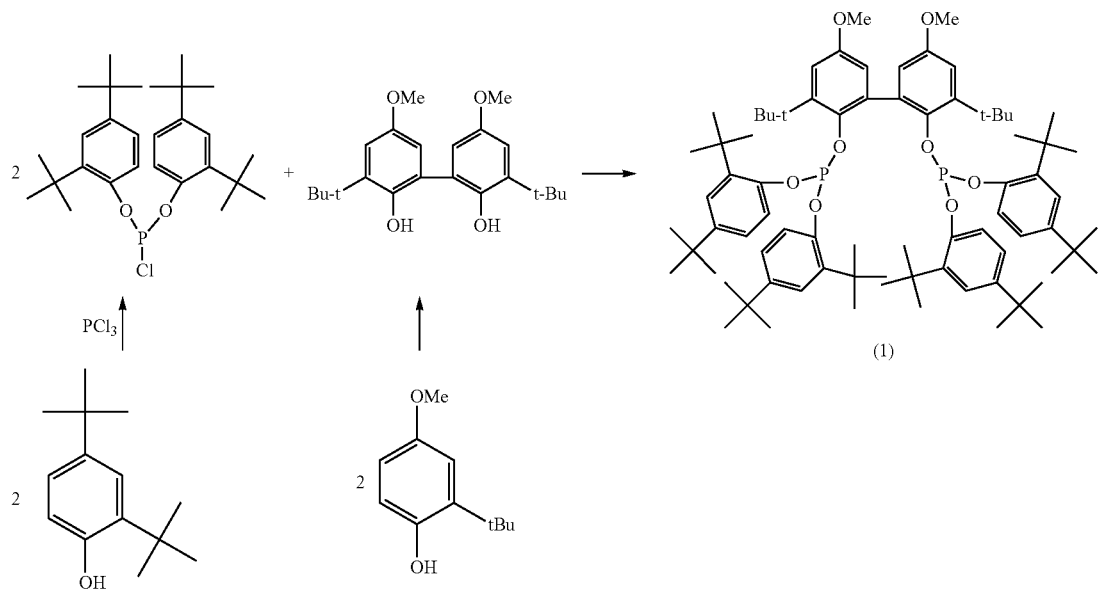

For workup, the triethylamine hydrochloride formed was filtered off and washed with 20 ml of dry toluene and the filtrate was concentrated to dryness under reduced pressure.
Result:
Mass: 41.5 g (yield 82%)

Preparation of 3,3'-di-tert-butyl-5,5'-dimethoxy-[1,1'-biphenyl]-2,2'-diyltetrakis(2,4-di-tert-butylphenyl)bis(phosphite)

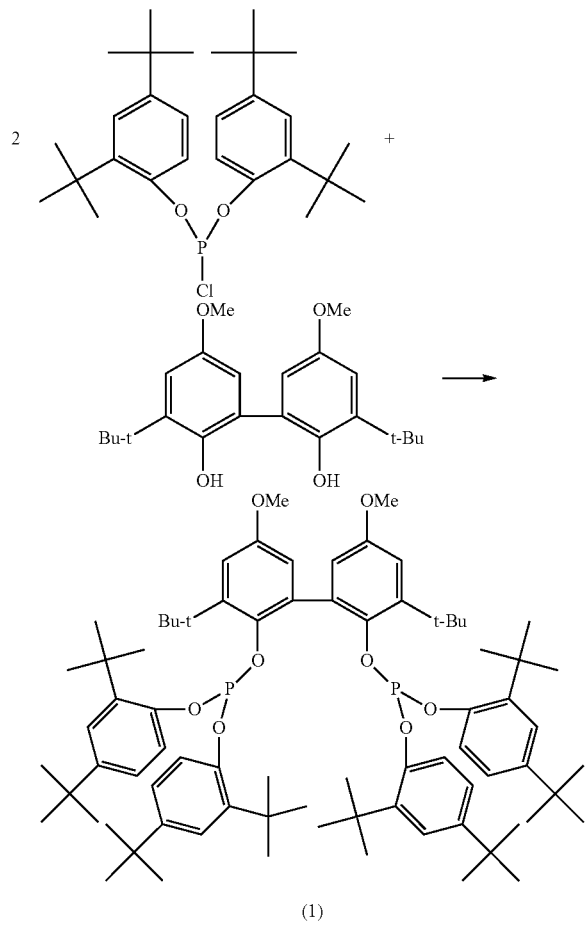

12.0 g of bis(2,4-di-tert-butylphenyl)chlorophosphite (0.021 mol) were dissolved in 100 ml of dry acetonitrile in a 250 ml Schlenk flask.

In a second Schlenk flask (250 ml), 3.2 g (0.009 mol) of 3,3'-di-tert-butyl-5,5'-dimethoxy-[1,1'-biphenyl]-2,2'-diol were added to 50 ml of dry acetonitrile and 2.2 g of degassed N,N-dimethylaminobutane (DMAS) with stirring. A suspension was formed here.

The biphenol/DMAB solution was then added dropwise at 0° C. to the chlorophosphite solution over 1 h. This was then warmed to room temperature overnight and then stirred at 55° C. for 12 hours. Subsequently the reaction solution was again cooled to room temperature and filtered. The solid was washed twice with 20 ml each time of dry acetonitrile and then dried under reduced pressure and analysed.

In order to separate the product from the tris(2,4-di-tert-butylphenyl)phosphite, the solid was transferred from the frit to a 500 ml Schlenk flask and 400 ml of dry acetonitrile were added. Subsequently, the Schlenk flask was heated to 60° C. for 5 h, the mixture was filtered while hot and washed once with 20 ml of dry acetonitrile.

The filtrate was concentrated under reduced pressure and analysed.

In order to further purify the product, 80 ml of dry acetonitrile were added to the Schlenk flask and the suspension was heated to 60° C. for 1.5 h and then filtered by frit while hot. The filtrate was subsequently concentrated under reduced pressure.

In order to remove the aminohydrochloride, the solid was dissolved in 20 ml of dry toluene, stirred at room temperature for ½ h and then filtered. The solid was washed twice with 10 ml of dry toluene. The filtrate was subsequently concentrated under reduced pressure and analysed.
Result:
Mass: 3.2 g (26.7% yield)
Procedure for the Catalysis Experiments
Experimental Description—General In a 100 ml autoclave from Parr Instruments, raffinate 3 was hydroformylated with the aid of synthesis gas (CO/$H_2$=1:1 (% by vol.)). Raffinate 3 is a mixture of: ca. 26% 1-butene, 32% trans-2-butene, 17% cis-2-butene, 25% n-butane and traces of isobutane and neopentane. As the precursor, Rh(acac)(CO)$_2$ was initially charged in toluene. The ligand was used in a molar excess of 4:1 relative to rhodium. Tinuvin 770DF was used as stabilizer in a molar ratio to the ligand of ca. 1:1. In addition, as GC standard, ca. 0.5 g of tetraisopropylbenzene (TIPB) was added. About 9 g of reactant were metered in after the reaction temperature envisaged had been attained.

During the reaction, the pressure was kept constant via synthesis gas regulation with a mass flow meter. The stirrer speed was 1200 min$^{-1}$. Samples were taken from the reaction mixture after 5 hours. The results of the experiments are summarized in Table 1.

Experimental Description—Specific

In a 100 ml autoclave from Parr Instruments, 8.8 g of raffinate 3 were hydroformylated at 128° C. and 43 bar synthesis gas pressure. As the precursor, Rh(acac)(CO)$_2$ (100 ppm Rh) was initially charged in 45 g of toluene. As the ligand, 0.107 g of ligand was used in the catalyst mixture solution. 0.057 g of Tinuvin 770DF was added as the organic amine, and 0.451 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 5 hours.

In Table 1 the hydroformylation results of raffinate 3 at 43 bar synthesis gas pressure and 128° C. are shown.

TABLE 1

| Entry | Ligand | Aldehyde yield in [%] | Regioselectivity n-pentanal in % |
|---|---|---|---|
| 1 | 1* | 82 | 43 |
| 2 | 2 | 54 | 99 |

*inventive compound

Definition of the Selectivity:

In hydroformylation, there is the n/iso selectivity: the ratio of linear aldehyde (=n) to branched aldehyde (=iso). In this case, the regioselectivity with respect to the n-aldehyde signifies that this amount of linear product was formed. The remaining percentage then corresponds to the branched isomer. Thus, at a regioselectivity of 50%, n-aldehyde and isoaldehyde are formed in equal proportions.

Using the compound (1) according to the invention, the regioselectivity compared to the comparative ligand (2) could be clearly approximated to the 50% mark, which is a balanced ratio of n-aldehyde and isoaldehyde.

The experiments carried out demonstrate that the objects presented are achieved by the compound (1) according to the invention.

The invention claimed is:

1. A compound of the formula (I):

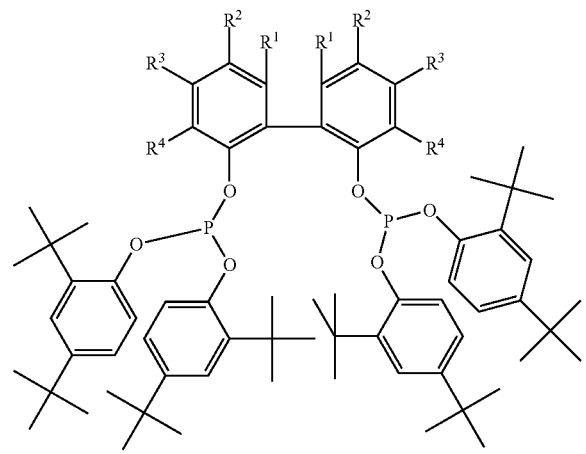

(I)

where
$R^1$, $R^3$, $R^4$ are selected from the group consisting of: —H, —($C_1$-$C_{12}$)-alkyl and —O—($C_1$-$C_{12}$)-alkyl, and
$R^2$ is —O—(C1-C12)-alkyl,
wherein the alkyl groups mentioned may be substituted as follows:
substituted —($C_1$-$C_{12}$)-alkyl groups and substituted —($C_1$-$C_{12}$)-alkoxy groups, depending on their chain length, may have one or more substituents; the substituents are mutually independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl;
and at least one of the $R^1$, $R^3$ and $R^4$ radicals is not —H.

2. The compound according to claim 1, where $R^4$ is not —H.

3. The compound according to claim 1, where $R^4$ is —($C_1$-$C_{12}$)-alkyl or —O—($C_1$-$C_{12}$)-alkyl.

4. The compound according to claim 1, where $R^4$ is —($C_1$-$C_{12}$)-alkyl.

5. The compound according to claim 1, where $R^2$ is —OMe.

6. The compound according to claim 1, where $R_4$ is -Me or -tBu.

7. The compound according to claim 1, where $R^4$ is -tBu.

8. The compound according to claim 1, according to the formula (1):

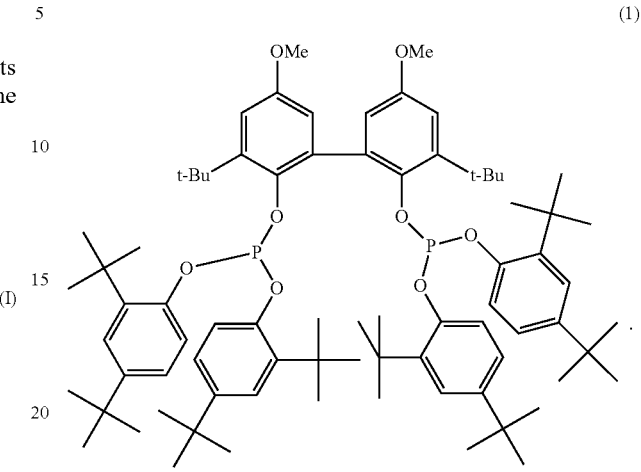

(1)

9. A process comprising the following process steps:
a) initially charging an olefin, forming a reaction mixture,
b) adding a compound according to claim 1 and a substance including a metal selected from: Rh, Ru, Co or Ir,
c) feeding in $H_2$ and CO,
d) heating the reaction mixture, wherein the olefin is converted to an aldehyde.

10. A complex according to the formula (II):

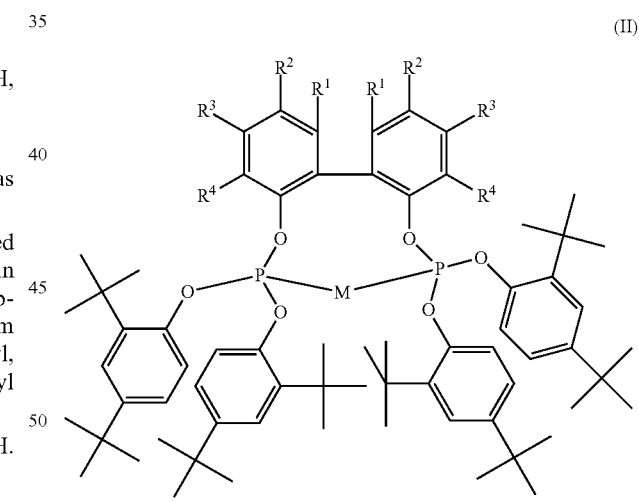

(II)

where
$R^1$, $R^2$, $R^3$ and $R^4$ are —H, —($C_1$-$C_{12}$)-alkyl or —O—($C_1$-$C_2$)-alkyl,
wherein the alkyl groups mentioned may be substituted as follows:
substituted —($C_1$-$C_{12}$)-alkyl groups and substituted —($C_1$-$C_{12}$)-alkoxy groups, depending on their chain length, may have one or more substituents; the substituents are mutually independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl;
and M is Rh, Ru, Co or Ir.

11. The complex according to the formula (III):

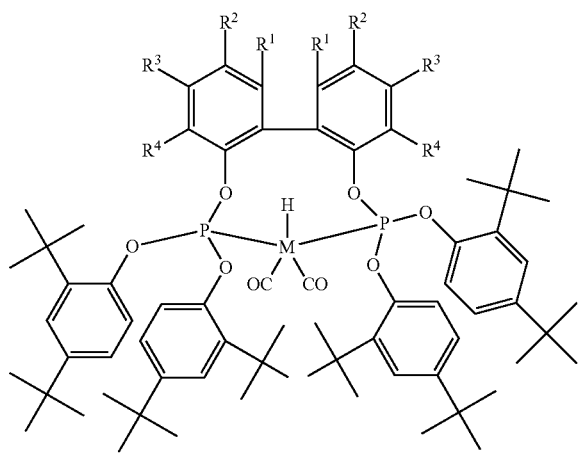

(III)

where
R$^1$, R$^2$, R$^3$ or R$^4$ are —H, —(C$_1$-C$_{12}$)-alkyl or —O—(C$_1$-C$_{12}$)-alkyl,
wherein the alkyl groups mentioned may be substituted as follows:
substituted —(C$_1$-C$_{12}$)-alkyl groups and substituted —(C$_1$-C$_{12}$)-alkoxy groups, depending on their chain length, may have one or more substituents; the substituents are mutually independently selected from —(C$_3$-C$_{12}$)-cycloalkyl, —(C$_3$-C$_{12}$)-heterocycloalkyl, —(C$_6$-C$_{20}$)-aryl, fluorine, chlorine, cyano, formyl, acyl or alkoxycarbonyl;
and M is Rh, Ru, Co or Ir.

12. The complex according to claim 10,
where M is Rh.

13. A process comprising the following process steps:
a) initially charging an olefin, forming a reaction mixture,
b) adding a complex according to claim 10,
c) feeding in H$_2$ and CO,
d) heating the reaction mixture, wherein the olefin is converted to an aldehyde.

* * * * *